US009161774B2

(12) United States Patent
Lauchner

(10) Patent No.: US 9,161,774 B2
(45) Date of Patent: Oct. 20, 2015

(54) ROTATABLE CUTTING INSTRUMENT

(71) Applicant: Kyphon SARL, Neuchatel (CH)

(72) Inventor: Craig E. Lauchner, Mountain View, CA (US)

(73) Assignee: KYPHON SARL, Neuchatel (CH)

( * ) Notice: Subject to any disclaimer, the term of this patent is extended or adjusted under 35 U.S.C. 154(b) by 307 days.

(21) Appl. No.: 13/829,258

(22) Filed: Mar. 14, 2013

(65) Prior Publication Data
US 2014/0276802 A1 Sep. 18, 2014

(51) Int. Cl.
A61B 18/00 (2006.01)
A61B 17/32 (2006.01)
A61B 17/3205 (2006.01)
A61B 18/14 (2006.01)

(52) U.S. Cl.
CPC ... *A61B 17/320068* (2013.01); *A61B 17/32002* (2013.01); *A61B 17/320016* (2013.01); *A61B 17/32053* (2013.01); *A61B 18/14* (2013.01); *A61B 2017/320024* (2013.01); *A61B 2018/00202* (2013.01); *A61B 2018/00339* (2013.01); *A61B 2018/00601* (2013.01)

(58) Field of Classification Search
CPC .................. A61B 18/00; A61B 17/320016
USPC ........................................................... 606/45
See application file for complete search history.

(56) References Cited

U.S. PATENT DOCUMENTS

| 4,649,919 | A | 3/1987 | Thimsen et al. |
| 5,123,904 | A | 6/1992 | Shimomura et al. |
| 6,001,116 | A | 12/1999 | Heisler et al. |
| 7,033,357 | B2 | 4/2006 | Baxter et al. |
| 7,641,667 | B2 | 1/2010 | Sample |
| 7,674,263 | B2 | 3/2010 | Ryan |
| 2002/0013579 | A1 | 1/2002 | Silvestrini |
| 2007/0027464 | A1* | 2/2007 | Way et al. ...................... 606/170 |
| 2007/0162062 | A1* | 7/2007 | Norton et al. .................. 606/170 |
| 2008/0103504 | A1* | 5/2008 | Schmitz et al. ................. 606/79 |
| 2010/0076476 | A1* | 3/2010 | To et al. ......................... 606/170 |
| 2011/0196401 | A1 | 8/2011 | Robertson et al. |
| 2011/0196405 | A1 | 8/2011 | Dietz |
| 2011/0288553 | A1* | 11/2011 | Jansen et al. .................... 606/83 |

* cited by examiner

*Primary Examiner* — Carl H Layno
*Assistant Examiner* — Jennifer Ghand
(74) *Attorney, Agent, or Firm* — Sorell Lenna & Schmidt LLP

(57) ABSTRACT

A surgical instrument includes a first member having an inner surface defining a first passageway. A second member is disposable within the first passageway and movable relative to the first member. The second member defines a longitudinal axis and extends between a first end and a second end configured to engage tissue. The second end includes a first surface configured for a non-penetrating engagement with the tissue and a second surface including at least two spaced apart cutting members extending axially from the first surface. The cutting members are rotatable to excise a portion of the tissue.

19 Claims, 2 Drawing Sheets

ROTATABLE CUTTING INSTRUMENT

TECHNICAL FIELD

The present disclosure generally relates to medical devices for the treatment of musculoskeletal disorders, and more particularly to a surgical system for tissue removal and a method for treating a spine.

BACKGROUND

Spinal stenosis typically occurs when the spinal cord, cauda equina and/or nerve root(s) are impinged by one or more tissues in the spine, such as a buckled or thickened ligamentum flavum. Impingement of neural and/or neurovascular tissue in the spine by a buckled or thickened ligamentum flavum may cause pain, numbness and/or loss of strength or mobility in one or both of a patient's lower limbs and/or of the patient's back.

In lumbar spinal stenosis (LSS), the space around the spinal cord becomes narrow, thus compressing the spinal cord and the nerve roots. This causes back pain with neurogenic claudication, i.e., pain, numbness, or weakness in the legs that worsens with standing or walking and is alleviated with sitting or leaning forward. Compression of neural elements generally occurs as a result of hypertrophied facet or ligamentum flavum hypertrophy. LSS is one of the most common reasons for back surgery and the most common reason for lumbar spine surgery in adults over 65 years of age. Patients suffering from spinal stenosis are typically first treated with conservative approaches such as exercise therapy, analgesics, anti-inflammatory medications, and epidural steroid injections. When these conservative treatment options fail and symptoms are severe, surgery may be required to remove impinging tissue and decompress the impinged nerve tissue.

Decompressive laminectomy, a well-known treatment for LSS, unroofs the spinal canal by resectioning posterior spinal elements, such as the ligamentum flavum and/or the facet adjacent to the lumbar nerve roots. Wide muscular dissection and retraction is needed to achieve adequate surgical visualization. The extensive resection and injury to the posterior spine and supporting muscles can lead to instability with significant morbidity, both post-operatively and longer-term. Spinal fusion may be required to reduce the resultant instability. Laminectomy may be used for extensive multi-level decompression.

Standard methods of cutting tissue may include using a scalpel and scissors or electrosurgical procedures using radio frequency energy. Electrosurgical procedures and techniques using radio frequency energy are currently used since they generally reduce patient bleeding and trauma associated with cutting operations. Additionally, electrosurgical ablation procedures, where tissue surfaces and volume may be reshaped, cannot be duplicated through other treatment modalities.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

A further disadvantage of using radio frequency energy is the generation of smoke. The smoke is malodorous and can contain airborne viral particles that may be infectious. Furthermore, the smoke often obscures visualization of the procedure. When the smoke becomes too dense, the procedure is delayed until the smoke is released through one of the trocar ports and after enough carbon dioxide gas has re-insufflated the abdominal cavity. This unnecessarily prolongs the operative time.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices is wide and flat, creating a relatively wide area of volumetric tissue removal and making fine dissections along tissue planes more difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient severing or cutting of nerve and/or soft tissue that can be used during a procedure, such as, for example, open decompression. Further, there is also a need for devices and methods that provide fine dissection capabilities of nerve and/or soft tissue. Devices and methods that do not cause a high level of collateral thermal damage and allow for the control of necrosis in the tissue being treated are also needed. Devices and methods that provide efficient, controlled and safe debulking of tissue would also be beneficial.

SUMMARY

In one embodiment, a surgical instrument is provided. The surgical instrument comprises a first member including an inner surface defining a first passageway. A second member is disposable within the first passageway and movable relative to the first member. The second member defines a longitudinal axis and extends between a first end and a second end configured to engage tissue. The second end includes a first surface configured for a non-penetrating engagement with the tissue and a second surface including at least two spaced apart cutting members extending axially from the first surface. The cutting members are rotatable to excise a portion of the tissue. Systems and methods are provided.

In one embodiment, a surgical instrument is provided. The surgical instrument comprises a cannula including an inner surface defining a passageway. A tubular shaft is disposable within the passageway and axially translatable relative to the cannula. The shaft defines a longitudinal axis and extends between a first end and a second end configured to engage a ligamentum flavum. The second end includes a distal face configured for a non-penetrating engagement with the ligamentum flavum and at least two spaced apart cutting blades extending axially from the distal face. The blades each include a tip configured to axially pierce the ligamentum flavum and the blades are rotatable relative to the cannula to excise a portion of the ligamentum flavum.

In one embodiment, a surgical instrument is provided. The surgical instrument comprises a first member including an inner surface defining a first passageway. A second member is disposable within the first passageway and movable relative to the first member. The second member defines a longitudinal axis and extends between a first end and a second end configured to engage a ligamentum flavum. The second end includes a distal face configured for a non-penetrating engagement with the ligamentum flavum and a second surface including at least two spaced apart cutting blades extending axially from the distal face. The cutting blades are rotatable to excise a portion of the ligamentum flavum. A third member is disposable within the first passageway and movable relative to the first member. The third member extends between a first end and a second end configured to penetrate laminae and form a cavity therein.

BRIEF DESCRIPTION OF THE DRAWINGS

The present disclosure will become more readily apparent from the specific description accompanied by the following drawings, in which.

DETAILED DESCRIPTION

Figure 1:
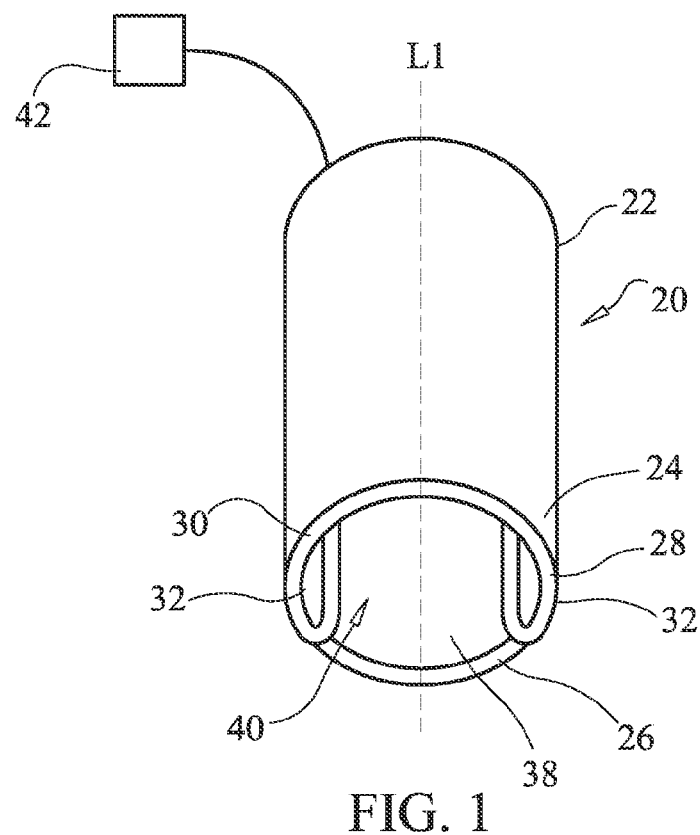
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system for tissue removal and a method for treating a spine. In some embodiments, the surgical system and method are employed using minimally invasive surgical techniques to achieve permanent lumbar decompression by removing a ligamentum flavum.

In one embodiment, the surgical system of the present disclosure is employed for resecting a ligamentum flavum to achieve lumbar decompression and avoids damaging dura mater. In some embodiments, the surgical system includes a cannula inserted adjacent a surgical site and tissue. A partial laminectomy can be performed using a circular ultrasonic bone saw or a trephine. In some embodiments, components of the surgical system create a circular access hole through the lamina to access the ligamentum flavum from a posterior approach. In some embodiments, the surgical system includes a cutter that is rotatable and punches through the ligamentum flavum but does not damage the dura. In some embodiments, upon disposal of the cutter through the ligamentum flavum, the cutter is rotated. The cutter includes blades having knife edges that cut an excised portion of the tissue, which comprises a circular hole in the ligamentum flavum. In some embodiments, the surgical system includes suction or other devices to remove the excised portion.

In one embodiment, the surgical system includes a rotating cutter that punches safely through the ligamentum flavum with a blunt point and/or a rounded shape. In some embodiments, the cutter is configured to not harm the dura and is self-limiting in depth because of the geometry of the circular cutter. In one embodiment, the cutter includes tips comprising knives. In some embodiments, the cutter is connected to an electrosurgical device to employ RF to core the ligamentum flavum.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
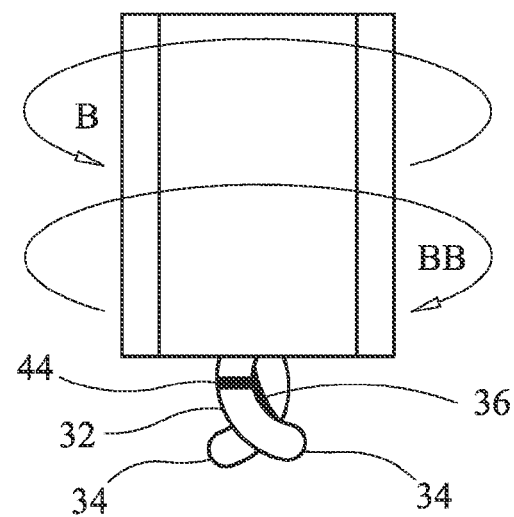
FIG. 2 is a side view of the components shown in FIG. 1.
Figure 3:
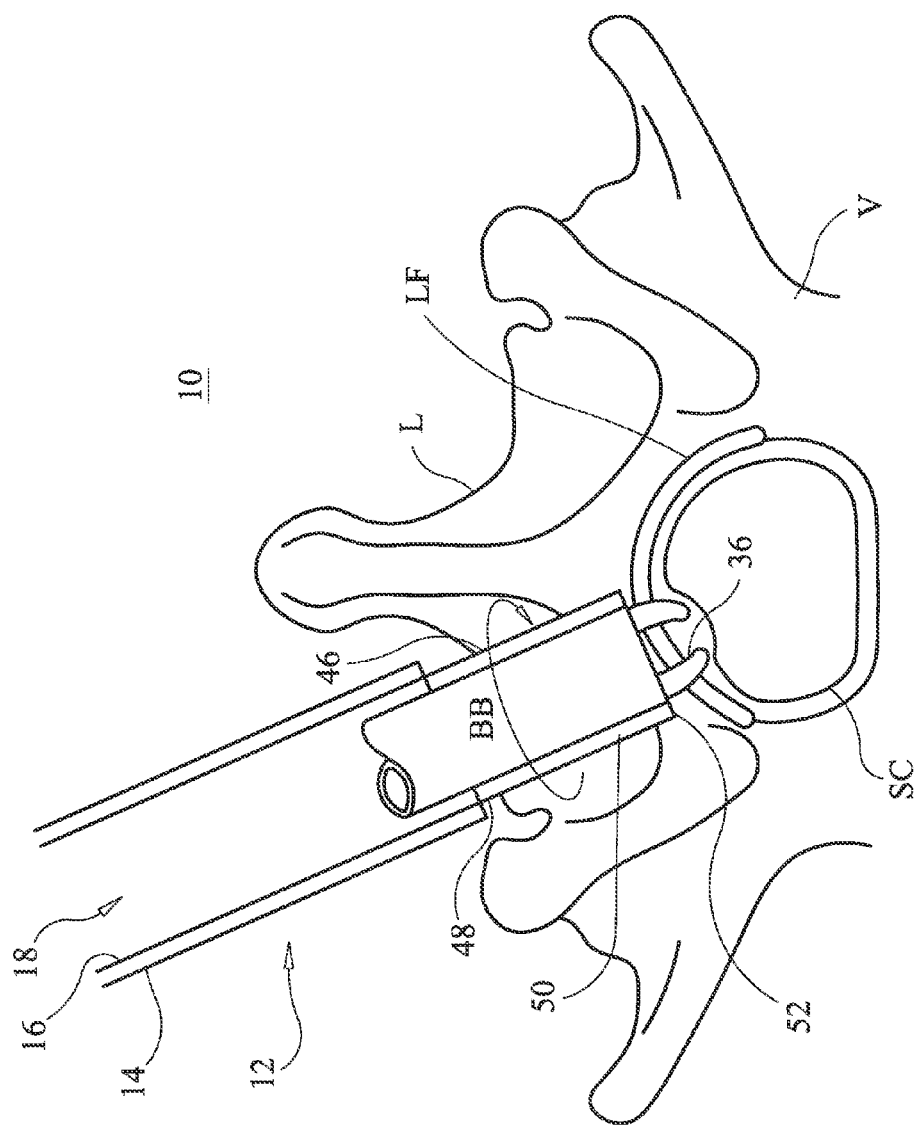
FIG. 3 is a plan view of components of one embodiment of a surgical system in accordance with the principles of the present disclosure disposed with vertebrae.

The following discussion includes a description of a surgical system including a surgical instrument, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there is illustrated components of a surgical system 10 including a surgical instrument 12.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a surgical instrument 12. Instrument 12 includes a first member, such as, for example a cannula 14. Cannula 14 includes an inner surface 16 defining a first passageway 18. Passageway 18 has a circular cross section configuration having a uniform diameter along the length of cannula 14. It is contemplated that passageway 18 has alternate cross section configurations, such as, for example, oval, oblong, triangular, square, hexagonal, polygonal, irregular, uniform, non-uniform and/or tapered. Cannula 14 has an outer diameter of approximately 10 mm and an inner diameter of approximately 5-8 mm. It is contemplated that cannula 14 has various inner and outer diameters according to a particular application. Passageway 18 is sized and dimensioned for disposal of a second member. Cannula 14 has an outer surface that is smooth or even to prevent injury to the anatomy of a patient, such as, for example, soft tissue, when instrument 12 is inserted through an incision and delivered to the surgical site. It is contemplated that all or only a portion of the outer surface of cannula 14 may have various surface configurations, such as, for example, rough, threaded, arcuate, undulating, porous, semi-porous, dimpled, polished and/or textured, to enhance fixation of cannula 14 with tissue. Cannula 14 is made of stainless steel. It is contemplated that cannula 14 is made of any combination of suitable materials provided in the present disclosure.

Instrument 12 includes a second member, such as, for example, a shaft 20. Shaft 20 has a tubular configuration along its length. It is contemplated that shaft 20 has various shapes, such as, for example, oval, oblong, triangular, square, hexagonal, polygonal, irregular, uniform, non-uniform and/or tapered. Shaft 20 is disposable within first passageway 18 and movable or axially translatable relative to cannula 14. Shaft 20 includes an inner surface 38 that defines a second passageway 40. Second passageway 40 is connected to a suction source 42 in a configuration to draw an excised portion of ligamentum flavum LF through second passageway 40. Shaft 20 has an opening at its distal end having a circular cross section configuration. It is envisioned that the opening may have alternate cross section configurations, such as, for example, oval, oblong, triangular, square, hexagonal, polygonal, irregular, uniform, non-uniform and/or tapered. As suction source 42 is actuated, a vacuum or suction is produced at the opening such that excised tissue is drawn out of the surgical site through passageway 40 of shaft 20.

Shaft 20 defines a longitudinal axis L1 and extends between a first end 22 and a second end 24. First end 22 is in fluid communication with suction source 42. End 22 of cutting member includes a drive portion (not shown) configured to rotate shaft 20 in the direction shown by arrow B and/or the direction shown by arrow BB. It is envisioned that the drive portion may be configured to engage an actuator, such as, for example, a surgical instrument, powered drill, hand drill, driver or other tool to rotate shaft 20, in the direction shown by arrow B and/or the direction shown by arrow BB. In one embodiment, drive portion has a hexagonal cross sectional configuration and is configured to engage a correspondingly shaped portion of the actuator. It is envisioned that the drive portion may include a square, triangular, polygonal, star or hexalobe cross sectional configuration configured engage a correspondingly shaped portion of the actuator.

Second end 24 is configured to engage soft tissue, such as, for example, ligamentum flavum LF. Second end 24 has a tubular configuration having a diameter of approximately 2 mm to 6 mm. It is contemplated that second end 24 has various configurations, such as, for example, those alternatives described herein. Second end 24 includes a first surface 26 configured for non-penetrating engagement with the ligamentum flavum LF and a second surface 28 configured for penetrating engagement with the ligamentum flavum LF.

First surface 26 includes a distal face 30 defined by the circumferential edge of shaft 20. Distal face 30 is planar so as to not cut tissue. Second surface 28 includes at least two spaced apart cutting members 32 extending axially along longitudinal axis L1 from distal face 30. Members 34 are blunt to push through the relatively taught ligamentum flavum and simultaneously protect the dura mater by not being sharp to penetrate it. Adjacent to members 34 are members 36 which are sharpened blades to cut ligamentum flavum with rotational motion.

Each cutting member 32 includes a blunt distal tip 34 configured to axially pierce the ligamentum flavum LF and not the dura of the spinal cord SC. In one embodiment, distal tip 34 is rounded. In one embodiment, distal tip 34 is shaped similarly to that of a Tuohy needle tip. The blunt distal tip 34 is specifically designed so as to be an atraumatic tip. That is, the blunt distal tip 34 is specifically designed so as to prevent or minimize damage to tissue as the device is used in situ. The blunt distal tip 34 can have different configurations such as circular, oval, arcuate, trapezoidal with rounded corners or any other configuration that would not damage tissue as the device is used in situ. The surface of the blunt distal tip 34 is non-abrasive so that it slides across tissue as the device is moved about at the surgical site and does not damage adjacent tissue.

Each cutting member 32 has a cutting blade 36 extending between distal face 30 and a portion of cutting member 32 proximal to distal tip 34. Cutting blades 36 are oriented in the circumferential plane of shaft 20. It is contemplated that blades 36 have various surface configurations, such as, for example, serrated, linear, straight, curved, convex, concave, continuous, intermittent, even, uneven and combinations thereof to facilitate cutting tissue.

Instrument 12 includes a third member, such as, for example, a bone cutter 46 disposable within first passageway 18 of cannula 14 and movable relative to cannula 14. Bone cutter 46 extends between a first end 48 and a second end 50 configured to penetrate laminae and form a cavity therein. In one embodiment, second end 50 includes an ultrasonic circular bone saw 52. In one embodiment, second end 50 includes a trephine 52.

In assembly, operation and use, system 10 is employed with a surgical procedure, such as, for example, a treatment of lumbar spinal stenosis. It is contemplated that one or all of the components of system 10 can be delivered or implanted as a pre-assembled device or can be assembled in situ. System 10 may be completely or partially revised, removed or replaced. It is envisioned that system 10 may also be used to treat other affected portions of the patient, such as, for example, a calcaneus bone, bones of the feet or hands, bones of the spine, bones of the arms and legs, etc.

In use, to treat lumbar spinal stenosis, the medical practitioner obtains access to a surgical site in any appropriate manner, such as through the skin, or through an incision and retraction of tissues. In one embodiment, a drill is employed to remove bone tissue to provide access to a repair site. It is envisioned that system 10 can be used in any existing surgical method or technique including open surgery, mini-open surgery, minimally invasive surgery and percutaneous surgical implantation. Once access to the surgical site is obtained, the particular surgical procedure can be performed for treating the injury or disorder. The configuration and dimension of system 10 is determined according to the configuration, dimension and location of a selected section of nerves and the requirements of a particular application.

An incision is made in the body of a patient and a cutting instrument (not shown) creates a surgical pathway for positioning of components of system 10. A preparation instrument (not shown) can be employed to prepare tissue surfaces, as well as for aspiration and irrigation of a surgical region according to the requirements of a particular surgical application.

Cannula 14 is positioned within the surgical pathway creating a working pathway to a lamina L of a vertebra V. Bone cutter 46 is axially translated through passageway 18 of cannula 14 such that bone cutter 46 engages lamina L. Bone cutter 46 is then activated to rotate relative to lamina L. In one embodiment, ultrasonic bone saw 52 is activated to perform a partial laminectomy to create a circular access hole through lamina L to access ligamentum flavum LF. In one embodiment, a partial laminectomy is performed by rotating trephine 52 to create a circular access hole through lamina L to access ligamentum flavum LF. After the access hole is created in lamina L, bone cutter 46 is withdrawn from cannula 14. Shaft 20 is then axially translated through passageway 18 of cannula 14 until distal tip 34 of cutting members 32 makes contact with ligamentum flavum LF. The practitioner then punctures through ligamentum flavum LF with the cutting members 32 using a downward motion until he or she feels an absence of resistance and distal face 30 is engaged with ligamentum flavum LF preventing further downward movement of cutting members 32. Once cutting members 32 have punctured through ligamentum flavum LF, the drive portion of end 22 is then activated by an activator, such as, for example, an electric motor to rotate cutting blades 36 in direction BB to excise a portion of ligamentum flavum LF. Cutting blades 36 rotate at least 180 degrees about longitudinal axis L1 forming a bore in ligamentum flavum LF. Suction source 42 is then activated to draw the excised portion through second passageway 40 out of the surgical site.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below. It is envisioned that system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application.

The components of system 10 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of system 10.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first member including an inner surface defining a first passageway;
a second member disposable within the first passageway and movable relative to the first member, the second member defining a longitudinal axis and extending between a first end and a second end configured to engage tissue, the second end including a first surface configured for a non-penetrating engagement with the tissue and a second surface including at least two spaced apart cutting members extending axially from the first surface, wherein the cutting members are rotatable to excise a portion of the tissue; and
a third member disposable within the first passageway and movable relative to the first member, the third member extending between a first end and a second end configured to penetrate laminae of the tissue and form a cavity therein.

2. A surgical instrument as recited in claim 1, wherein the second end of the third member includes an ultrasonic bone saw.

3. A surgical instrument as recited in claim 1, wherein the second end of the third member includes a trephine.

4. A surgical instrument as recited in claim 1, wherein the first member includes a cannula.

5. A surgical instrument as recited in claim 1, wherein the second member includes an inner surface that defines a second passageway connected to a suction source in a configuration to draw the excised portion through the second passageway.

6. A surgical instrument as recited in claim 1, wherein the second end of the second member has a tubular configuration.

7. A surgical instrument as recited in claim 1, wherein the second end of the second member is rotatable relative to the first member such that the cutting members are rotatable to excise the portion of the tissue.

8. A surgical instrument as recited in claim 1, wherein each of the cutting members includes an arcuate configuration.

9. A surgical instrument as recited in claim 1, wherein each of the cutting members is configured to be RF enabled to cut the tissue.

10. A surgical instrument as recited in claim 1, wherein the first surface includes a planar face.

11. A surgical instrument comprising:
a first member including an inner surface defining a first passageway; and
a second member disposable within the first passageway and movable relative to the first member, the second member defining a longitudinal axis and extending between a first end and a second end configured to engage tissue, the second end including a first surface configured for a non-penetrating engagement with the tissue and a second surface including at least two spaced apart cutting members extending axially from the first surface, wherein the cutting members are rotatable to excise a portion of the tissue;
wherein each of the cutting members includes a blade and a tip, the tip being configured to axially pierce the tissue and the blade being rotatable to excise the portion of the tissue.

12. A surgical instrument as recited in claim 11, wherein the tip has a blunt configuration.

13. A surgical instrument comprising:
a cannula including an inner surface defining a passageway; and
a tubular shaft disposable within the passageway and axially translatable relative to the cannula, the shaft defining a longitudinal axis and extending between a first end and a second end configured to engage a ligamentum flavum,
the second end including a distal face configured for a non-penetrating engagement with the ligamentum flavum and at least two spaced apart cutting blades extending axially from the distal face, wherein the blades each include a tip configured to axially pierce the ligamentum flavum and the blades are rotatable relative to the cannula to excise a portion of the ligamentum flavum.

14. A surgical instrument as recited in claim 13, wherein each of the cutting blades is configured to be electrically energized to cut the ligamentum flavum.

15. A surgical instrument as recited in claim 13, wherein the tip has a blunt configuration.

16. A surgical instrument comprising:
a first member including an inner surface defining a first passageway; and
a second member disposable within the first passageway and movable relative to the first member, the second member defining a longitudinal axis and extending between a first end and a second end configured to engage a ligamentum flavum, the second end including a distal face configured for a non-penetrating engagement with the ligamentum flavum and a second surface including at least two spaced apart cutting blades extending axially from the distal face, wherein the cutting blades are rotatable to excise a portion of the ligamentum flavum; and a third member disposable within the first passageway and movable relative to the first member, the third member extending between a first end and a second end configured to penetrate laminae and form a cavity therein.

17. A surgical instrument as recited in claim 16, wherein the second end of the third member includes an ultrasonic bone saw.

18. A surgical instrument as recited in claim 16, wherein the second end of the third member includes a trephine.

19. A surgical instrument as recited in claim 16, wherein each of the cutting blades is configured to be electrically energized to cut the ligamentum flavum.

* * * * *